United States Patent
Grohn (10) Patent No.: US 10,695,213 B2
(45) Date of Patent: Jun. 30, 2020

(54) SYSTEM FOR CRYOTHERAPY (71) Applicant: OY Cryon Ltd., Nummenkyla (FI)

(72) Inventor: Martti Grohn, Tallinn (EE)

(73) Assignee: OY CRYON LTD., Nummenkyla (FI)

( * ) Notice: Subject to any disclaimer, the term of this patent is extended or adjusted under 35 U.S.C. 154(b) by 66 days.

(21) Appl. No.: 16/062,324

(22) PCT Filed: Aug. 5, 2016

(86) PCT No.: PCT/FI2016/050551
§ 371 (c)(1),
(2) Date: Jun. 14, 2018

(87) PCT Pub. No.: WO2017/103325
PCT Pub. Date: Jun. 22, 2017

(65) Prior Publication Data
US 2018/0369014 A1    Dec. 27, 2018

(30) Foreign Application Priority Data
Dec. 16, 2015 (FI) ...................................... 20150362

(51) Int. Cl.
*A61F 7/00* (2006.01)
*F25D 3/10* (2006.01)

(52) U.S. Cl.
CPC ............ *A61F 7/0053* (2013.01); *F25D 3/102* (2013.01); *A61F 2007/0096* (2013.01)

(58) Field of Classification Search
CPC ............ A61F 2007/0096; A61F 7/0053; A61F 7/00–2007/126; F25D 3/102; A61H 2201/02–2201/107

(Continued)

(56) References Cited

U.S. PATENT DOCUMENTS 4,344,291 A * 8/1982 Tyree, Jr. ................ A23L 3/361
62/168
8,162,930 B2 * 4/2012 Brojek .................. A61F 7/0053
606/20

(Continued)

FOREIGN PATENT DOCUMENTS

DE    3441091    5/1986

OTHER PUBLICATIONS

Written Opinion of corresponding PCT App. No. PCT/FI2016/050551 completed Nov. 8, 2016.

(Continued)

*Primary Examiner* — Gary Jackson
*Assistant Examiner* — Jonathan T Kuo
(74) *Attorney, Agent, or Firm* — Emerson Thomson Bennett; Roger D. Emerson; Peter R. Detorre (57) ABSTRACT

An invention concerns a moisture control in a cryotherapy system and creating of snow mist. The system comprises a treatment chamber for at least one person, a closable entry to the treatment chamber, and a cooling apparatus. The cooling apparatus comprises an evaporator configured to function with a coolant and a valve for flow control of the coolant, wherein the evaporator is placed in the treatment chamber and the valve is coupled to the evaporator. The system further comprises a ventilation aperture for obtaining an additional air into the treatment chamber, the ventilation aperture being placed far from the evaporator to such spot that the additional air flows from the ventilation aperture towards the centre of the treatment chamber and simultaneously mixes with an air included in the treatment chamber so that water vapour of the additional air changes from gas to solid ice crystals and forms snow mist in the treatment chamber.

7 Claims, 7 Drawing Sheets

(58) Field of Classification Search
USPC .................................................. 607/81–87
See application file for complete search history.

(56) References Cited

U.S. PATENT DOCUMENTS

| | | | | |
|---|---|---|---|---|
| 8,316,652 B2* | 11/2012 | Decourcelle | ............. | B60P 3/14 |
| | | | | 62/53.2 |
| 2014/0000307 A1* | 1/2014 | Fuhr | ...................... | F25D 3/102 |
| | | | | 62/452 |
| 2015/0265460 A1 | 9/2015 | Erganokov | | |
| 2016/0089262 A1* | 3/2016 | Kuehne | ................ | A61F 7/0053 |
| | | | | 606/20 |
| 2016/0361195 A1* | 12/2016 | Kuehne | ................ | A61F 7/0053 |

OTHER PUBLICATIONS

International Search Report of corresponding PCT App. No. PCT/FI2016/050551 dated Nov. 16, 2016.

\* cited by examiner

SYSTEM FOR CRYOTHERAPY

Technical field: an invention relates generally to producing cryogenic air (icy cold or extremely cold air) and cryotherapy for human beings. The invention especially relates to a manner by which the cryogenic temperature is produced.

BACKGROUND OF THE INVENTION

Cryotherapy is a therapy method in which a human body is treated 1-4 minutes with cold (such as −110° C.). The treatment has been proven to soothe pain for few hours and the treatment may reduce inflammation, for example, in rheumatism. A recurring cold treatment is assumed to increase a human body's ability to reduce toxic radicals of oxygen and thus also improve the health and capability. The cold treatment is gradually increased so that a person to be treated to is finally guided to a chamber providing a cryogenic temperature. A swimsuit, a mask covering a mouth and nose, a beanie or some other headwear, cloves, and footwear are used as clothing.

Various technologies are usable for creating cryogenic air. A liquid nitrogen technology is based on use of nitrogen and an evaporator. In more detail, a treatment chamber comprises an evaporator in which the liquid nitrogen evaporates and simultaneously takes heat from its environment and cools the treatment chamber. The price of a liquid nitrogen cooling apparatus is relative low but the transportation of the liquid nitrogen requires special arrangements and thus the usage costs of the apparatus are relative high. Another problem related to use of nitrogen is that the door of the treatment chamber may freeze to the door frame and the evaporator may also freeze. Removing of the ice causes maintenance outages.

Forming of the ice can be effectively avoided by using a compressor and a closed coolant circulation in cooling. When the cooling apparatus comprises two or more coolant circulations, the technique is termed a cascade-compressor technique. By using this technique −120° C. or even colder temperature is achieved so that air is circulated air in the treatment chamber. As an end result, the air is extremely dry and thus unpleasant to inhale and a person to be treated is forced to use a mask covering the person's mouth and nose in order to ease inhalation.

DE19515287C2 is mentioned as an example of a publication that describes the cascade-compressor technique. The following publications are mentioned as examples of the prior art: U.S. Pat. No. 8,316,652B2 "System and method for whole-body cryotherapy", U.S. Pat. No. 8,162,930B2 "Method and the device for cryogenic therapy applied on the whole body of a patient", CN100501273C "Controllable temperature deep cooling processing system based on self supercharging cryogenic fluids conveying technology", KR1011222B1 "Cooling machine using cold air", KR453113Y1 "Cryogenic of freezing device", and CN203065526U "Large-scale workpiece cryogenic treatment equipment".

In publication US2015265460A1 a valve for equalizing pressure is placed at a wall of a treatment chamber in the proximity of the ceiling. When the valve is located in this manner, air flowing through it hits in the treatment chamber to the evaporator and the moisture included in the air freezes on the surface of the evaporator.

The inventor of the present invention has expressed in magazine articles an idea of such hybrid system that utilizes a cooling implemented with a compressor technique as well as a cooling implemented with the liquid nitrogen technique.

A moisture control in a cryotherapy system is mentioned as one technical challenge in the invention. In more detail, there is a need to affect the composition of the air and in the same time forming of solid ice is aimed to be avoided.

SUMMARY OF THE INVENTION

An object of the invention is to solve the above-mentioned technical challenge. The invention also relates to producing a snow mist. The snow mist is created when the moisture (water vapour) included in air changes form from gas to into microscopic ice crystals. When a human being inhales snow mist, the ice crystals melt at which time it is easy to inhale and no mask is needed.

The invention concerns a system for cryotherapy, the system comprising a treatment chamber for at least one person, a closable entry to the treatment chamber, and a cooling apparatus comprising an evaporator configured to function with a coolant and a valve for flow control of the coolant, the evaporator being placed in the treatment chamber and the valve being coupled to the evaporator.

The system further comprises a ventilation aperture for obtaining an additional air into the treatment chamber, the ventilation aperture being placed far from the evaporator to such spot that the additional air flows from the ventilation aperture towards the centre of the treatment chamber and simultaneously mixes with an air included in the treatment chamber so that water vapour of the additional air changes from gas to solid ice crystals and forms snow mist in the treatment chamber, and the system is configured to create the snow mist in response to opening the valve and flowing of the coolant into the evaporator so that a liquid nitrogen is used as the coolant.

In one embodiment the system comprises a secondary cooling apparatus and the valve is to be opened when due to use of the secondary cooling apparatus the air included in the treatment chamber is cooled down to a predetermined temperature.

In one embodiment the system comprises such mid-chamber which includes an entry to the treatment chamber and an aperture for obtaining the additional air through the mid-chamber into the treatment chamber.

In one embodiment the system comprises such vestibule which includes an entry to the mid-chamber and a vent for obtaining the additional air through the vestibule into the mid-chamber.

In one the system comprises a ventilation hatch, the ventilation hatch preventing in its closed position flowing of the additional air into the treatment chamber.

In one embodiment the ventilation hatch is configured to be opened from its closed position before opening of the valve.

In one embodiment the ventilation hatch is placed to one of the following spots: a door, between the door and a door frame, an outer wall of the system, another surface between the treatment chamber and a space surrounding the treatment chamber.

In one embodiment the system comprises a piping for the coolant, the piping comprising a curved part whose wall thickness is greater than in a straight part of piping.

In one embodiment the system comprises a liquid nitrogen generator and the system is configured to receive an ambient air and to produce the liquid nitrogen to be used as the coolant from the ambient air.

The invention further concerns use of the system in a cryogenic treatment.

In one embodiment, the use aims to activate brown fat in a human body.

BRIEF DESCRIPTION OF THE DRAWINGS

For a more complete understanding of examples and embodiments of the present invention, reference is now made to the following descriptions taken in connection with the accompanying drawings in which.

DETAILED DESCRIPTION OF THE INVENTION

It is appreciated that the following embodiments are exemplary. Although the specification may refer to "one" or "some" embodiment(s), the reference is not necessarily made to the same embodiment(s), or the feature in question may apply to multiple embodiments. Single features of different embodiments may be combined to provide further embodiments.

Certain conditions are required to create snow mist. The snow mist is created when vapour changes to microscopic ice crystals. Because the ice crystals melt in a human being's inhalation system and moisture the inhaled air, it is more pleasant to inhale the air including snow mist than such air from which the ice crystals are missing. Therefore, a person to be treated does not need a mask in a treatment chamber when the treatment chamber contains enough snow mist.

Ventilation for cryotherapy should be implemented so that vapour included in air changes in the therapy room to ice crystals and form snow mist. Let us first examine air ventilation in a home, or air ventilation in some other space intended for living. An exhaust air and a make-up air are terms which are used in association with a living space. In forced ventilation the air to be removed from the living space is termed the exhaust air. The wall of the living space may include a make-up air vent through which the exhaust air is replaced with the make-up air when a ventilation device sucks air through an exhaust air vent out of the living space. Instead of the negative pressure created by the ventilation device the make-up air can be forced into the living space through a make-up channel. In the both arrangements a portion of air comes into the living space through the make-up air vent, or an aperture arranged in a window, and a portion of air leaves the living space through the exhaust vent.

In a treatment chamber for cryotherapy the ventilation vents are unnecessary because they may freeze so that air cannot pass through them. Another relevant difference between the treatment chamber according to the invention and a living space is that the make-up air and the exhaust air can flow through the same ventilation aperture into the treatment chamber and out from it. In the following the ventilation of the treatment chamber and the moisture control in the cryotherapy are described in details.

Figure 1A:
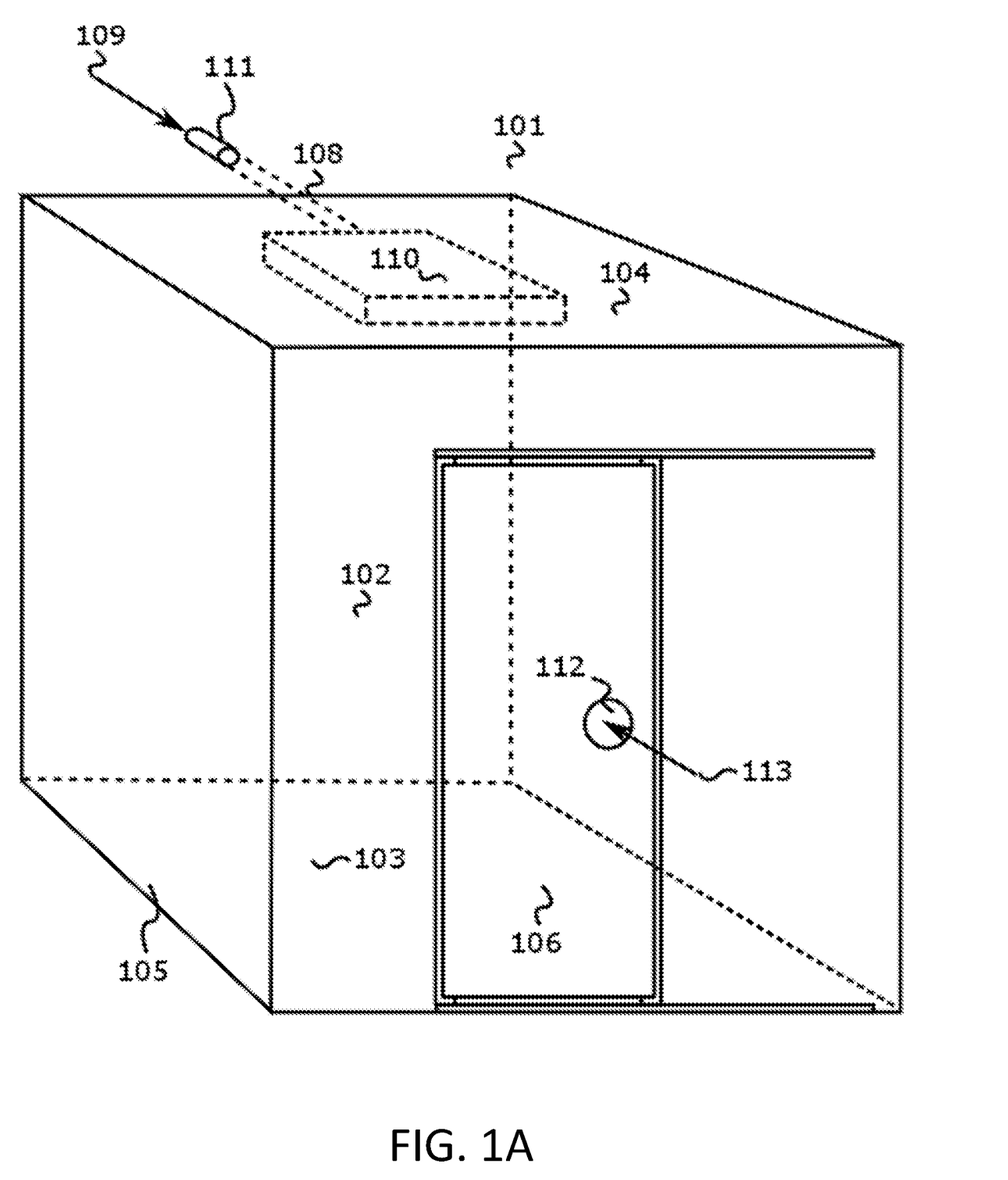
FIG. 1A shows a system for cryotherapy.

FIG. 1A shows a system 101 for cryotherapy. System 101 comprises a treatment chamber 102 that is limited by a floor 103, a roof 104, and at least one wall 105. Treatment chamber 102 may include corners (as in FIG. 1A) or it may has a shape of cylinder or cupola. Treatment chamber 102 is intended for at least one person and it includes a closable entry 106. Entry 106 is a door entry through which a person to be treated is received into treatment chamber 102 and after the treatment the person leaves treatment chamber 102. System 101 may comprise two cooling apparatus but in FIG. 1A system 101 is configured to operate with one cooling apparatus 108.

Cooling apparatus 108 includes at least one evaporator that functions with coolant 109. A valve 111 is coupled to cooling apparatus 108 to adjust the flow of coolant 109. Valve 111 may be attached directly to an evaporator 110. Alternatively, valve 111 is attached to a pipe through which coolant 109 flows into evaporator 110 when valve 111 is in its open position. Valve 111 may be an automated valve or a manual valve.

An air accessing into treatment chamber 102 can be termed a make-up air but that term may be misleading, because air is not leaving treatment chamber 102 when the air included in treatment chamber 102 is cooled. During the cooling, a portion of air is flowing through a ventilation aperture 112 into the treatment chamber, thus the portion of air flowing into treatment chamber 102 is termed an additional air 113. When liquid nitrogen is used as the coolant the air inside the treatment chamber becomes rapidly colder a number of degrees, due to which a plenty of additional air 113 flows through ventilation aperture 112 into the treatment chamber. If the flow of additional air 113 were hindered, a vacuum would be formed into treatment chamber 102 because air condenses when it cools. The phase of the snow mist creation starts when valve 111 is opened and coolant 109 flows into evaporator 110. When a required temperature is reached valve 111 will be closed.

A body of each person to be treated warms the air inside treatment chamber 102 due to which the air warms and expands and a portion of the air flows through ventilation aperture 112 out from treatment chamber 102. Physically, a temperature difference between system 101 and its environment aims to get even. In addition, treatment chamber 102 warms up when a sliding door 106 closing entry 106 is opened. The temperature increase, however, happens slowly when comparing it to the rapid temperature decrease in the snow mist creation phase.

The flow of additional air 113 into treatment chamber 102 is based on Gay-Lussac's law. This thermodynamic law is also known as Charles's law and it describes in which manner an ideal gas having a fixed mass acts in a constant pressure (isobaric process). Gay-Lussac's law is expressed as a formula:

$$\frac{V_1}{T_1} = \frac{V_2}{T_2}.$$

The formula can be applied to the air inside treatment chamber 102 so that $V_1$ is the volume of the air and $T_1$ is the temperature of the air at time moment 1 when valve 111 is opened and liquid nitrogen or a corresponding coolant 109 flows into evaporator 110. Correspondingly, $V_2$ is the volume of the air inside treatment chamber and $T_2$ is the temperature of the air later, at time moment 2, when treatment chamber 102 is reached a certain cryogenic temperature. Before opening valve 111 it can be assumed that temperature $T_1$ is essentially the same, for example 20° C., inside treatment chamber 102 and outside of it. Opening of valve 111 causes rapidly a great temperature difference $(T_1-T_2)$ between the air inside treatment chamber 102 and the air outside of it.

Figure 1B:
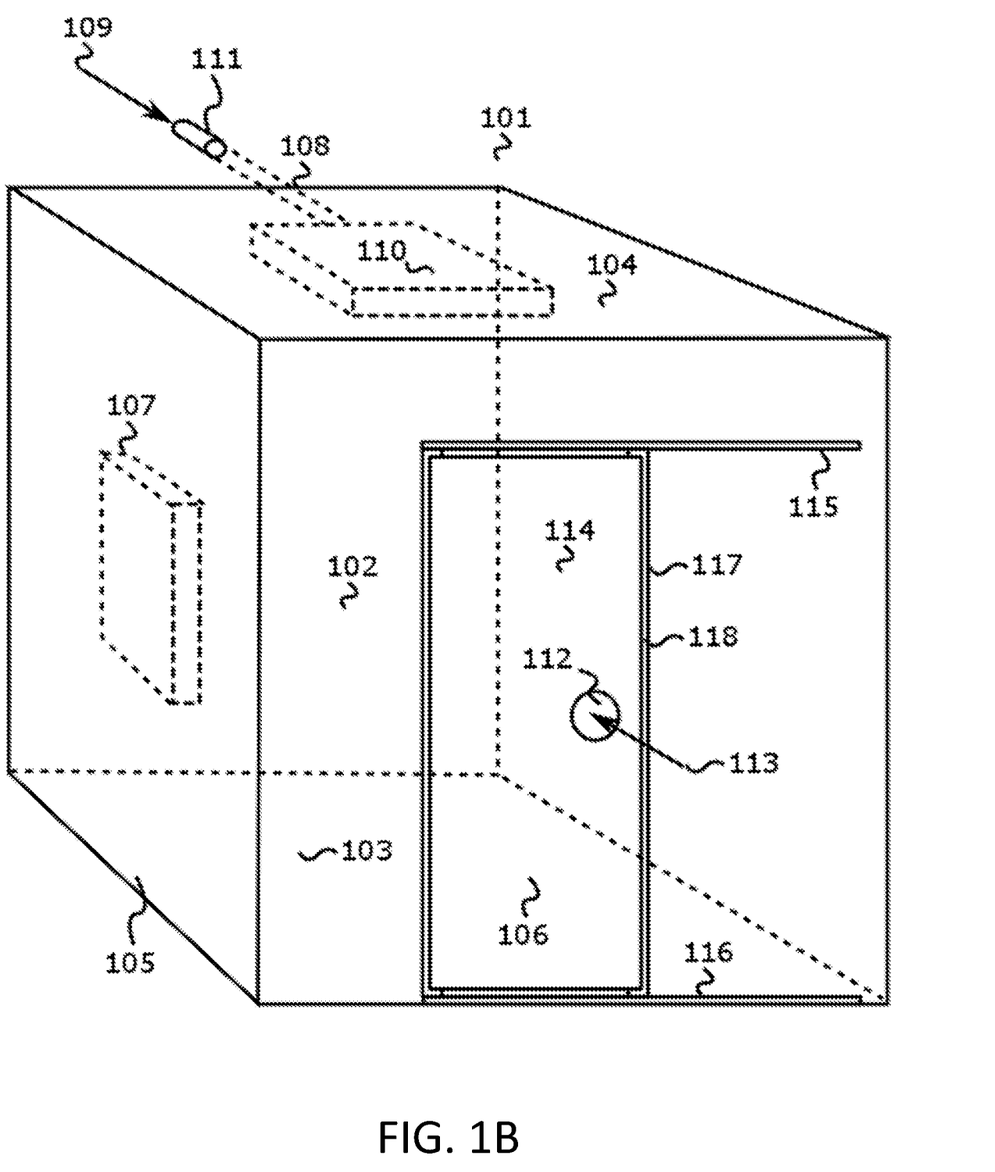
FIG. 1B shows a system comprising two cooling apparatus.

FIG. 1B shows system 101 comprising two cooling apparatus 107, 108. Cooling apparatus 107 is termed a secondary cooling apparatus, because it does not create snow mist, or it creates less snow mist than cooling apparatus 108. System 101 is adapted to create snow mist into treatment chamber 102 in response to opening valve 111 and flowing of coolant 109 into evaporator 110 included in cooling apparatus 108. In one embodiment second cooling evaporator 107 comprises at least one compressor and a closed coolant circulation. For example, RS-23 and RS-404A are appropriate coolants for secondary cooling apparatus 107.

In one embodiment treatment chamber 102 is cooled by secondary cooling apparatus 107 to a predetermined temperature, for example, to −90° C., and not until then cooling apparatus 108 is taken into use. By acting this way, system 101 can be economically used assuming that transporting of liquid nitrogen is relatively expensive.

In one embodiment a cryogenic temperature is maintained by secondary cooling apparatus 107 when the cryogenic temperature is already reached by means of cooling apparatus 108. This way of acting also saves the liquid nitrogen.

The duration of the snow mist creation phase depends on a starting temperature and a required top temperature. If valve 111 is opened at −90 Celsius (the starting temperature) and is closed at −110 Celsius (the required top temperature), the snow mist creation phase typically lasts one hour. After the snow mist creation phase treatment chamber 102 includes snow mist and it can be typically used for cryogenic therapy six hours. Because a person to be treated stays in the treatment chamber at most 4-5 minutes at a time, a number of people can be treated within the six hours.

Let us assume that the before mentioned formula (related to Gay-Lussac's law) is applied with $T_1$ value −90° C. and $T_2$ value −110° C. In Kelvin grade these temperatures are approximately 183 K and 163 K. Let us assume that at time moment 1 the volume of the treatment chamber is 15 m³ and volume $V_1$ of the air inside the treatment chamber 102 is the same, i.e. 15 m³. Therefore, at time moment 2, volume $V_2$ of the air is:

$$V_2 = V_1 \cdot (T_2/T_1) = 15 \text{ m}^3 \cdot (163 \text{ K}/183 \text{ K}) \approx 13.3 \text{ m}^3.$$

The amount of additional air 113 is obtained from the following subtraction:

$$V_1 - V_2 = 15 \text{ m}^3 - 13.3 \text{ m}^3 \approx 1.7 \text{ m}^3 \text{ i.e. } 1700 \text{ l}.$$

By using different values $V_1$, $V_2$, $T_1$, and $T_2$ a different end result is obtained, but in any case the amount of additional air 113 flowing to treatment chamber 102 is quite great. The additional air explains why the oxygen concentration of the air is high in cryogenic therapy. When a normal oxygen concentration is 20%, the oxygen concentration of treatment chamber 102 is even 22%. Cryogenic air is thicker than, for example, the air inside a building of residence and thus the cryogenic air includes more oxygen, nitrogen, argon, and other air substances in relation to the volume of the air.

Ventilation aperture 112 should be large enough to obtain additional air 113 through it into treatment chamber 102. In the example shown in FIG. 1 ventilation aperture 112 is a round hole having a diameter 20 cm, wherein the round hole is formed in a sliding door 114. Ventilation aperture 112 operates also as a handset so that sliding door 114 can be moved between an upper slide and an under slide by pulling from it.

In one embodiment sliding door 114 is hanging with Teflon-covered rollers from an upper slide 115 and the lower part of sliding door 114 includes guiding rolls that run in an under slide 116.

A door frame 117 limiting entry 106 is intentionally made so large that on each side of sliding door 114 there is at least 2 cm wide slot between door frame 117 and sliding door 114 when entry 106 is closed with sliding door 114. This slot 118 operates as ventilation aperture 112.

The shape of the ventilation aperture has no matter assuming that the ventilation aperture is large enough to enable an unobstructed air flow from outside of system 101 into treatment chamber 102 or to the opposite direction. If the area of ventilation aperture 112 is too small or it is too thin, ventilation aperture 112 may freeze so that air cannot pass it, or the ice in ventilation aperture 112 causes annoying whistle. There may be more than one ventilation apertures, for example, round hole 112 in sliding door 114 and rectangular slot 118 between sliding door 114 and door frame 117.

Ventilation aperture 112, 118 should be located far enough from evaporator 110 to such spot that addition air 113 mainly flows past evaporator 110 so that a minimum amount of water vapour included in additional air 113 freezes to the surface of evaporator 110 and forms there solid ice. Ventilation aperture 112, 118 should be placed so that additional air 113 mainly flows towards the centre of treatment chamber 102 and simultaneously mixes with the air included in the treatment chamber causing the water vapour included in additional air 113 to change to ice crystals, which forms (as much as possible) snow ice into treatment chamber 102. System 101 has an effective thermal insulation, thus it can be placed outdoors. The outdoor temperature and humidity has a great importance how great amount of the snow ice is created in treatment chamber 102.

Alternatively, system 101 can be placed indoor, into a building or space, where the temperature and humidity has minor changes regardless the current season or time of day. System 101 can be placed, for example, into a space in which the air temperature is 20-22° C. and the relative humidity of the air is (on average) 25-45%.

When system 101 comprises two cooling apparatus 107, 108, there may be several usage options when the cooling apparatus 108 intended for creating the snow mist is taken into use. Generally speaking, valve 111 is adapted to be opened when the air temperature in treatment chamber 102 is 173-213 K (i.e. from −100° C. to −60° C.).

Figure 2:
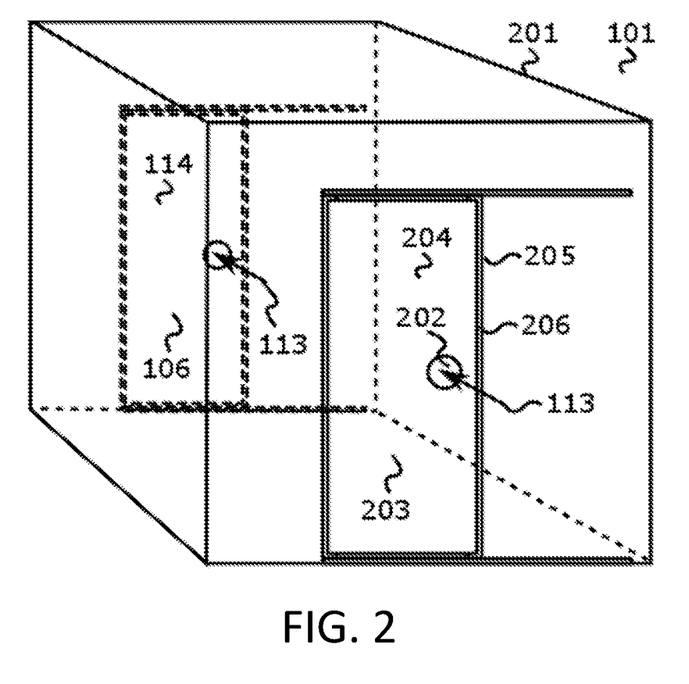
FIG. 2 shows a mid-chamber included in a system.

FIG. 2 shows a mid-chamber 201 for system 101. A person to be treated waits in mid-chamber 201 before entering through entry 106 into treatment chamber 102. The air temperature of mid-chamber 201 is, for example, −60° C.

Mid-chamber 201 prevents escaping of cryogenic air from treatment chamber 102, but some amount of the cryogenic air escapes from treatment chamber 102 when door 114 is open and the person to treated moves from mid-chamber 201 to treatment chamber 102 or returns from there. Mid-chamber 201 comprises a ventilation aperture 202 to obtain additional air 113 through mid-chamber 201 into treatment chamber 102.

In this example, entry 203 to mid-chamber 201 is closable by the same kind of sliding door 204 by which entry 106 is closable. In addition to aperture 202 formed in the sliding door, additional air 113 also flows into mid-chamber through a slot 206 locating between a door frame 205 and sliding door 204. When slot 206 is 2 cm wide and it extends over the 200 cm high and 75 cm wide sliding door, the area of slot 206 is 1100 cm². Therefore, slot 206 is larger than aperture 202 which is $\pi r^2$ i.e. 314 cm².

Figure 3:
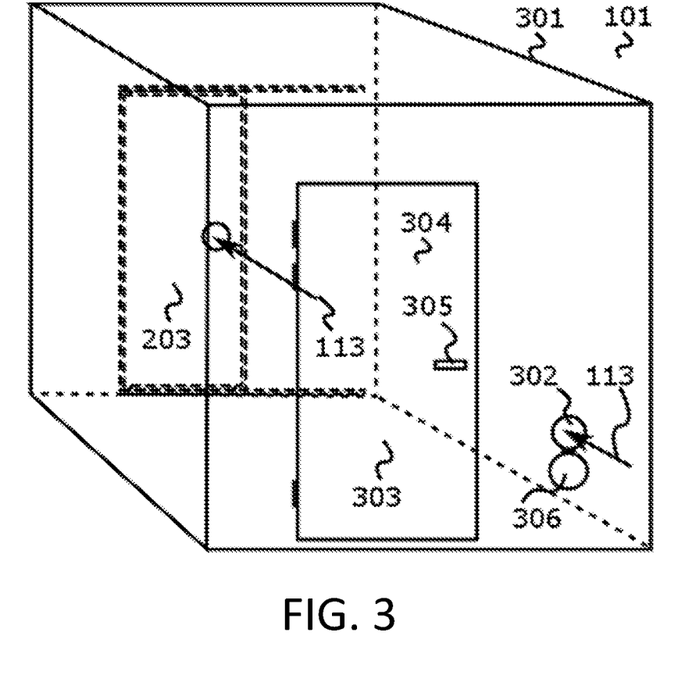
FIG. 3 shows a vestibule included in a system.

FIG. 3 shows a vestibule 301 which is included in system 101 and which comprises an entry 203 to mid-chamber 201. The temperature of vestibule 301 is, for example, −30° C. to prepare a person to be treated for coldness so that he/she is ready to move into even colder mid-chamber 201. Vestibule 301 comprises a ventilation aperture 302 to obtain additional air 113 outside of system 101 into vestibule 301. In this example entry 303 to the vestibule is closable with a door 304 having hinges and a door handle 305.

The door frame of door 304 includes an electrical resistor to prevent the door from freezing. Solid ice on door 304 as well as on other parts of system 101 is a problem that appears after the snow mist creation phase when air flows from treatment chamber 102 and through mid-chamber 201 and vestibule 301 out from system 101.

In one embodiment system 101 comprises a hinged ventilation hatch that hinders in its closed position flowing of additional air 113 through vestibule 301 and mid-chamber 201 into treatment chamber 102. Thus, the ventilation hatch helps to keep the cold air inside system 101. In FIG. 3 a ventilation hatch 306 is in the open position and additional air 113 may flow through aperture 302 into vestibule 301. Ventilation hatch 306 is adapted to be opened from its closed position before opening valve 111, i.e. before the snow mist creation phase. In the end of the snow mist phase valve 111 will be closed but evaporator 110 is still very cold and causes the creation of snow mist.

The flowing of additional air 113 into treatment chamber 102 ends when the temperature of treatment chamber does not anymore reduce. Then it is an appropriate point of time to close aperture 302 with ventilation hatch 306, because in response to rising of the air temperature the air begins to flow to the opposite direction, i.e. through vestibule 301 and aperture 302 out from system 101. When aperture 302 is closed with ventilation hatch 306 there is some amount of excess pressure in system 101. The excess pressure vanishes when door 304 is opened for a person to be treated.

Figure 4:
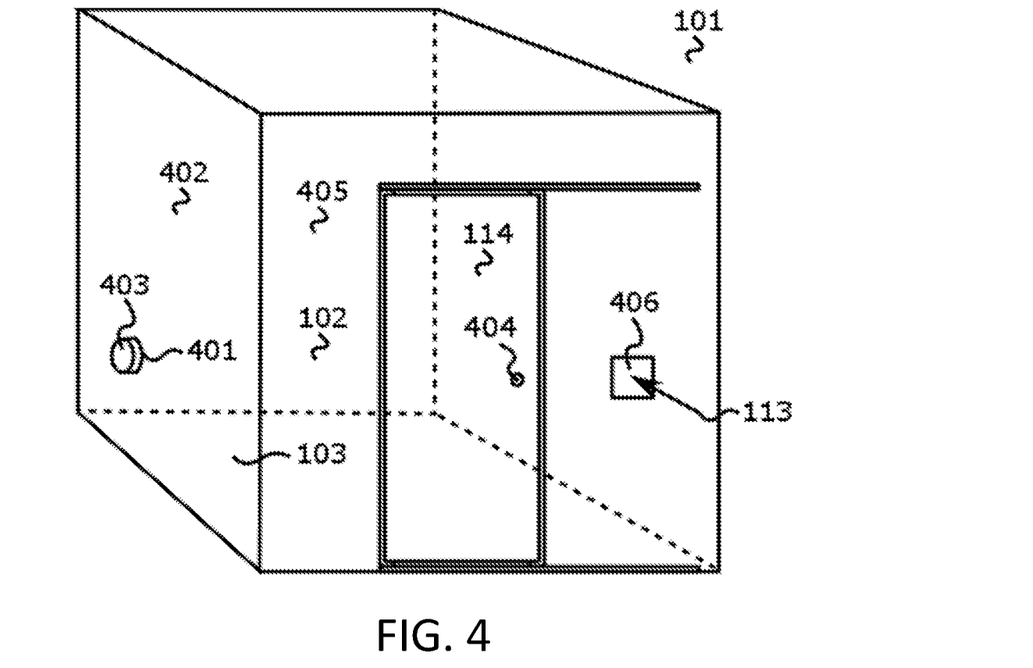
FIG. 4 shows alternative locations for a ventilation aperture and hatch.

FIG. 4 shows optional locations for the ventilation apparatus and ventilation hatch. A ventilation aperture 401 can be placed on outer wall 402 of system, for example, on treatment chamber 102. Aperture 401 is closed with a ventilation hatch 403, i.e. hatch 403 is in the closed position. Sliding door 114 is modified so that a knop 404 operates as the door handle. A square aperture 406 is located on a dividing wall 405 approximately at the height of knob 404, wherein the dividing wall separates treatment chamber 102 from the other system space. Dividing wall 405 is an example of another surface on which a ventilation aperture of system 101 can be located. The ventilation aperture of system 101 is large enough when the ventilation aperture does not freeze and become obstructed, i.e. it stays open during the use of treatment chamber 102.

Figure 5:
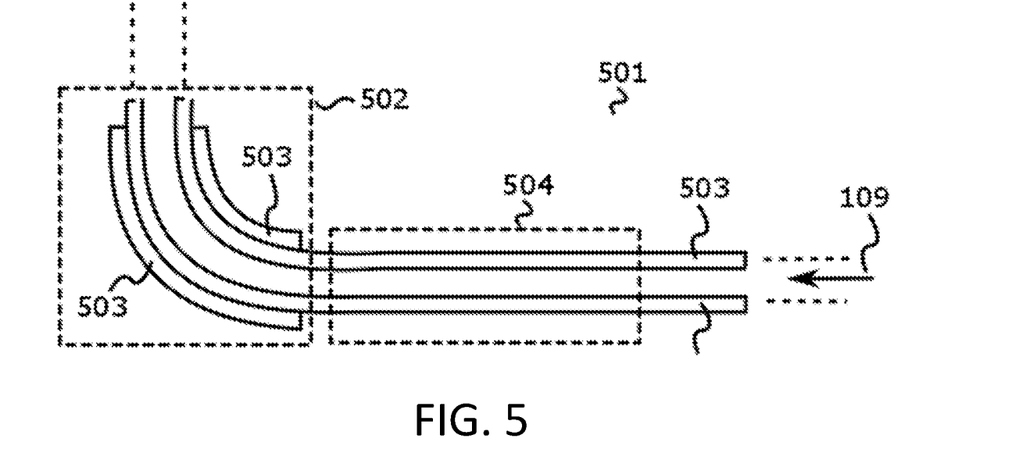
FIG. 5 shows strengthening the coolant piping.

FIG. 5 shows strengthening of coolant piping 501. Piping 501 is included in cooling apparatus 108 that creates cryogenic air and snow mist. Piping 501 is intended to conduct coolant 109 into evaporator 110 and the length of piping may be a number of meters comprising straight parts and curved parts. Piping 501 can be manufactured, for example, copper, aluminium, or stainless steel. Copper is a cost-effective material but especially the curved parts of piping 501 has been detected to corrode when coolant 109 flows in piping 501. The corrosion happens on the inner surface of the curved parts and finally causes a leak to piping 501. In order to avoid the leaks it is advisable to strengthen the curved parts of the piping. In the example shown in FIG. 5 piping 501 includes a curved part 502 where the thickness of a wall 503 is greater in a straight part 504 of piping 501. Curved part 502 can be implemented with two nested pipes. Alternatively, curved part 502 can be implemented using such pipe whose wall thickness is greater than in straight part 504. For example, the wall thickness could be 0.7 mm in straight part 504 and 1.0 mm in curved part 502.

Figure 6A:
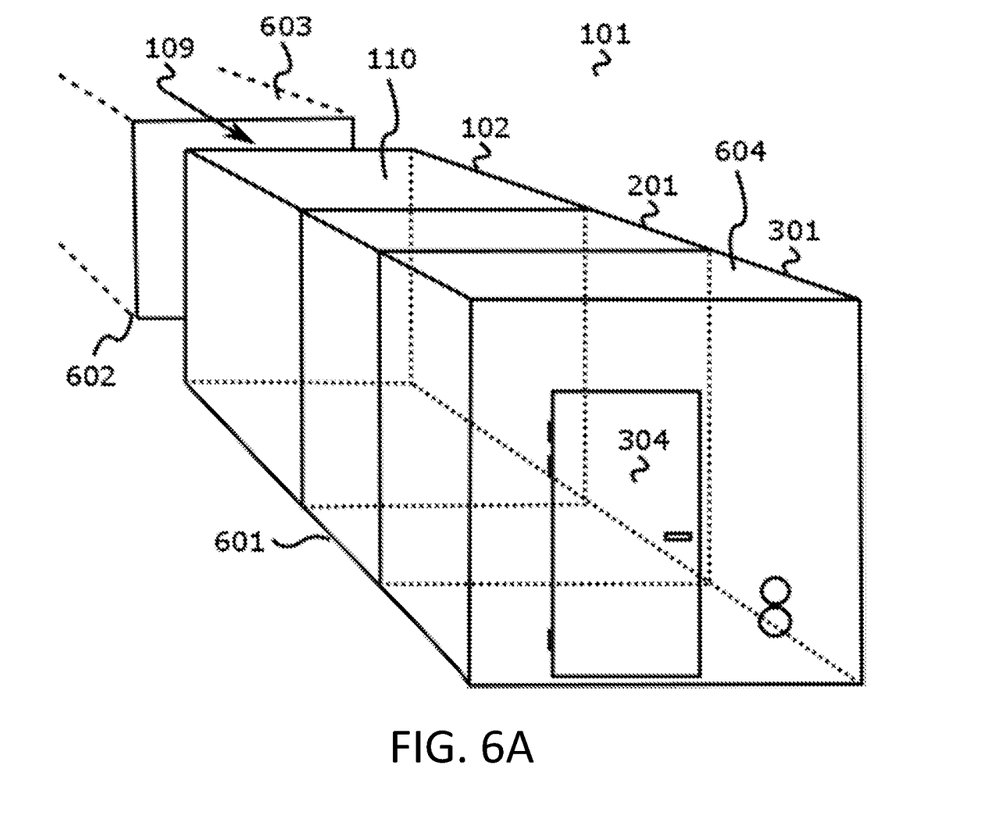
FIG. 6A shows a therapy unit with three chambers and a technical unit.

FIG. 6A shows a treatment unit 601 with three chambers and a technical unit 602. Treatment unit 601 is an example of system 101 in accordance with the invention, wherein vestibule 301 is the first chamber, mid-chamber 201 is the second chamber, and treatment chamber 102 is the third chamber. Treatment unit 601 may be size of a container and it can be transported to a delivery address as an ordinary cargo, for example, on a truck. In one embodiment system 101 further comprises technical unit 602 that includes apparatus needed for the cryotherapy. These apparatus comprises the cascade compressors for secondary cooling apparatus 107 and/or a liquid nitrogen generator 603.

A benefit of liquid nitrogen generator 603 is that the liquid nitrogen is obtained economically, without any transportation costs, from the nitrogen of the atmosphere. Also technical unit 602 can be built as the size of a container in order to move it easily to a delivery address. In the delivery address needed joints are made between treatment unit 601 and technical unit 602 and those joints are thermally insulated.

A connection pipe through which coolant 109 flows from technical unit 602 into evaporator 110 is mentioned as one example of the joints between treatment unit 601 and technical unit 602. Evaporator 110 is placed on the roof 604 of treatment unit 601. The floor, the walls, and roof 604 of treatment unit 601 should be isolated, for example, with polyurethane layer whose thickness is 150 mm (type USPU 150/LA). The outer surface of the isolation layer is covered with a sheet metal, fibreglass, or covered plywood. The cover of the outer surface is attached to the isolation layer, for example, with 2-component clue developed by Kiilto Oy. This clue remains elastic even in cryogenic conditions up to −160° C., and because the clue is elastic, it enables the (thermal) expansion. In addition, the cover material of the inner surface is attached with the clue. The clue is also used for sealing the grout joints of the inner surface. Covered plywood (thickness 12-20 mm), without any paint on it, is used as the inner surface of the treatment unit. Covered plywood to be used at the floor should have a patterned surface to avoid sliding of people.

Resistors (12 V/60 W) can be installed between the external door 304 of treatment unit 601 and the door frame to prevent freezing of the door (to the closed position). Alternatively, a sliding door can be used as the external door.

Figure 6B:
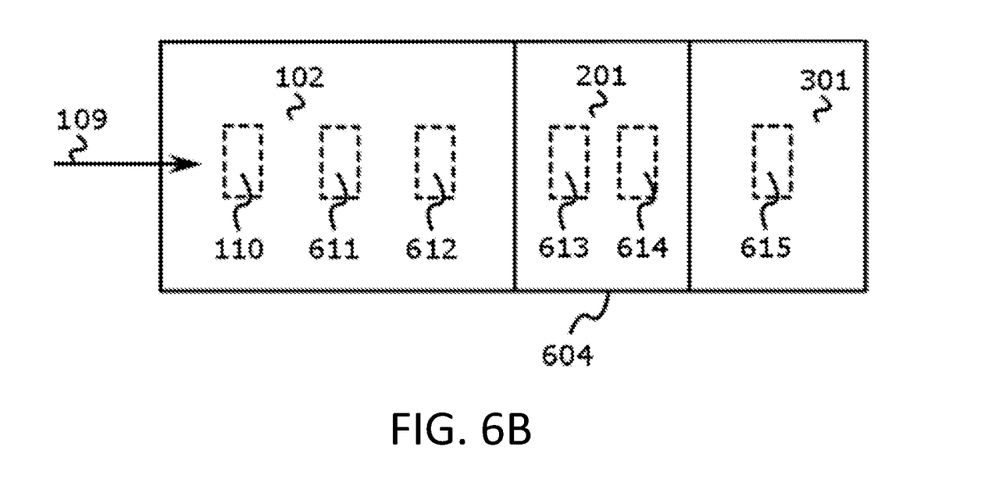
FIG. 6B shows from a bird's perspective the roof of a therapy unit.

FIG. 6B shows roof 604 of treatment unit 601 from a bird's perspective. Altogether six evaporators 110, 611-615 are placed to the inner roof so that the roof of treatment chamber 102 includes three evaporators 110, 611, 612, and two evaporators 613, 614 are placed on the roof of mid-chamber 201, and one evaporator 615 is placed on the roof of vestibule 301. The evaporators are connected to each other with connection pipes and to the coolant accumulator but the connection pipes are not drawn in the figure.

Cryogenic air is needed in treatment chamber 102, thus the most evaporators are placed there. In addition, coolant 109 arrives first to treatment chamber 102 and creates there snow mist. Coolant 109 flows then through evaporators 110, 611, 612 to mid-chamber 201. On the way through the evaporators in mid-chamber 201 coolant 109 warms up more and changes from liquid to gas but is still capable to cool also vestibule 301 before leaving treatment unit 601. When liquid nitrogen is used as coolant 109 the nitrogen changed to the gas can be released to the atmosphere.

In one embodiment evaporators 110, 611-615 are used by cooling apparatus 108 and secondary cooling apparatus 107 so that the coolants of cooling apparatus 108 and secondary cooling apparatus 107 circulates in their own circuits. This type of apparatus can be termed a hybrid cooling apparatus. An advance of the hybrid cooling apparatus is a smaller number of evaporators 110, 611-615 when comparing the number of evaporators to the embodiment shown in FIG. 1B, wherein evaporator 110 is used only by coolant apparatus 108 and secondary cooling apparatus 107 uses its own evaporator. Because the smaller number of evaporators, the hybrid cooling apparatus reduces the investment costs and saves space in treatment unit 601.

Figure 7A:
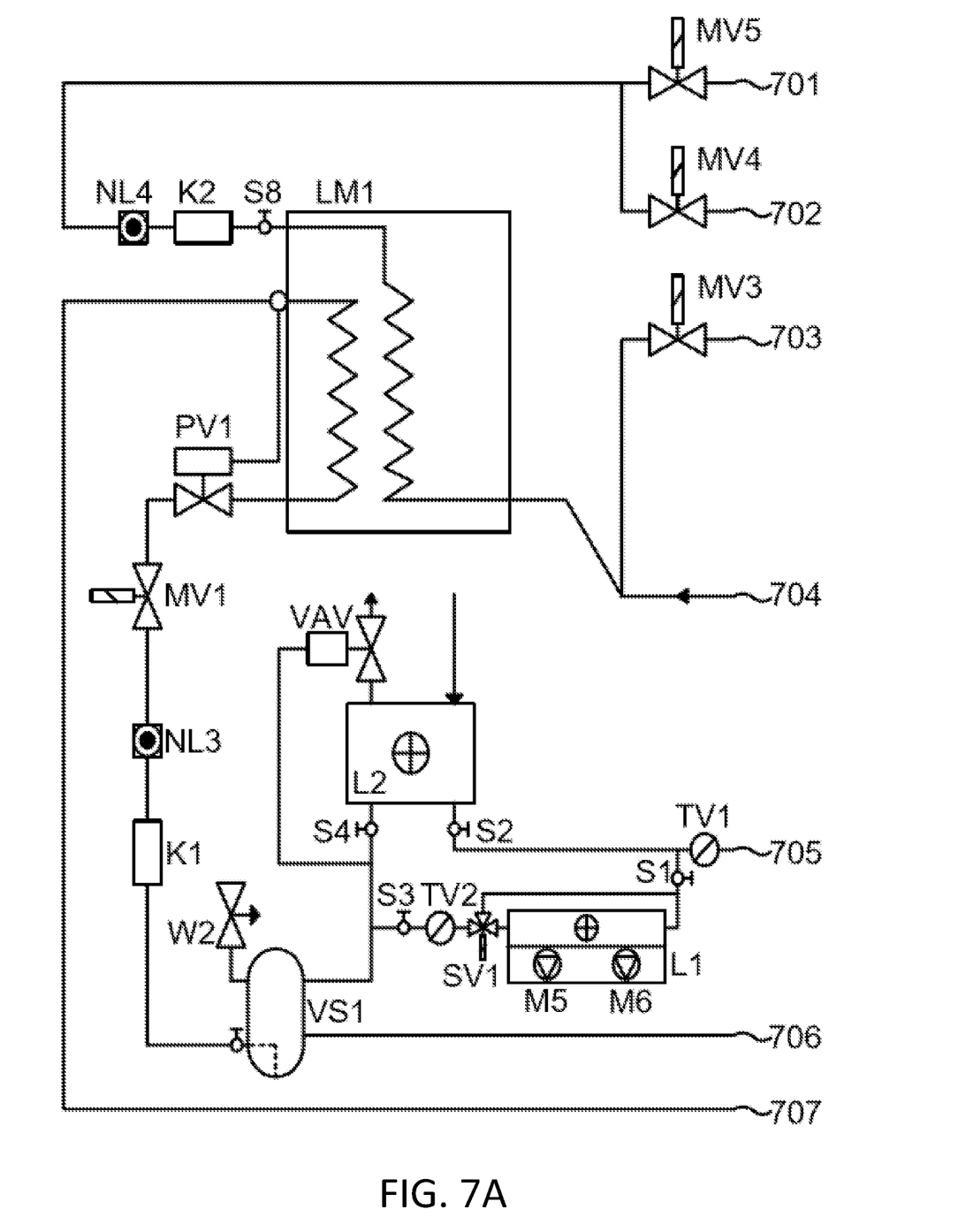
FIG. 7A shows a first part of a cooling apparatus schema.
Figure 7B:
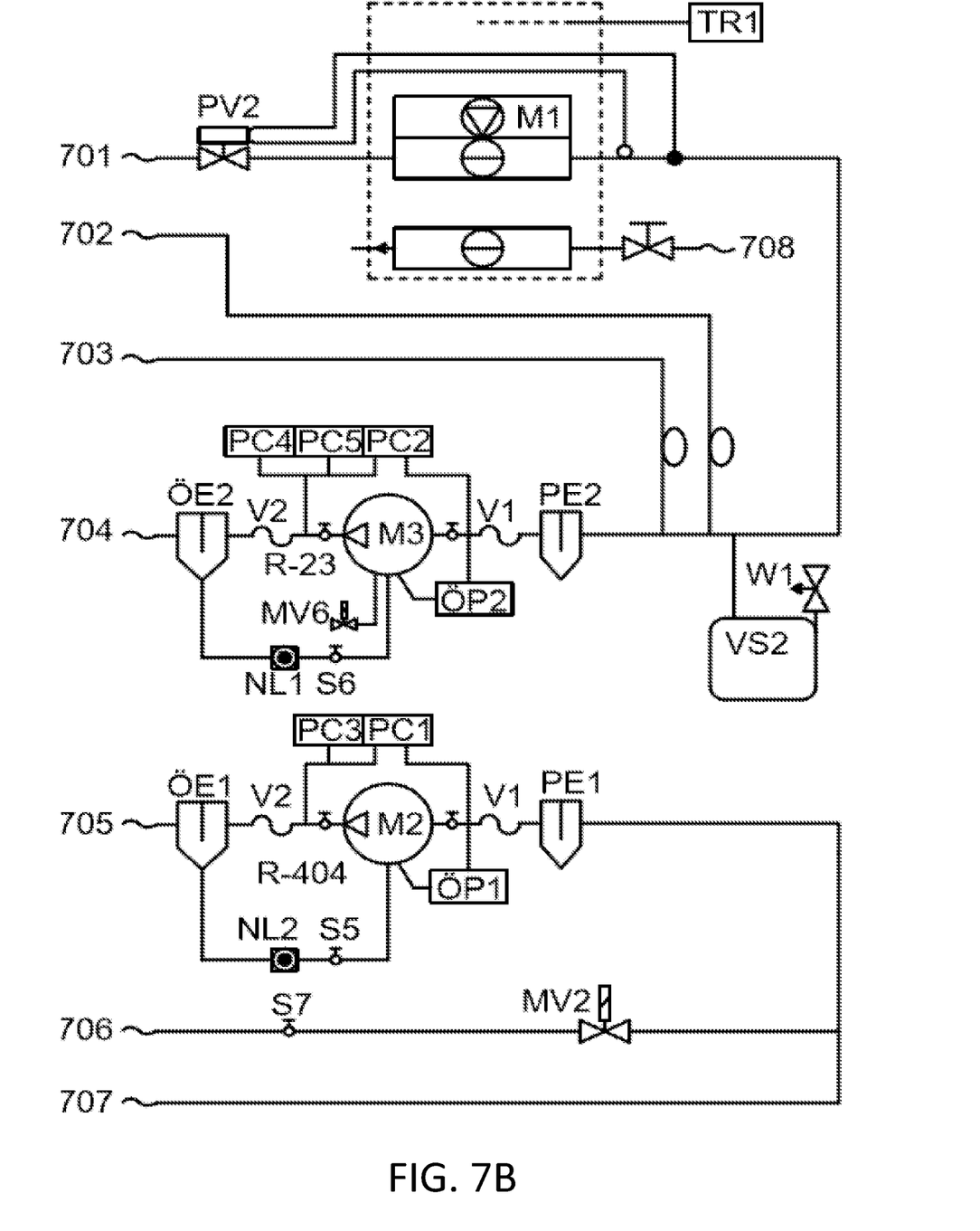
FIG. 7B shows a second part of a cooling apparatus schema.

FIG. 7A shows the first half of a chart that describes cooling apparatus 108 and secondary cooling apparatus 107. FIG. 7B shows the second half of the chart so that pipes 701-707 connect the apparatus parts together. The below list of the components of secondary cooling apparatus 107 relates to FIG. 7A as well as FIG. 7B:

M2 Compressor, 1. circuit
M3 Compressor, 2. circuit
V1, V2 Vibration isolator
ÖE1, ÖE2 Oil separator
NL1, 2 Sight glass
S5, 6 Shut-off valve
ÖP1, 2 Oil pressure switch
TV1 Setback valve
S1, S2, S3, S4 Shut-off valve
TV2 Setback valve
VAV Valve for water
L2 Condenser with plate heat exchanger
SV1 3-way magnet valve
L1 Air condenser
M5, M6 Blower motor
VS1, VS2 Liquid accumulator
W1, W2 Safety valve
K1, K2 Coolant dryer
NL2, NL4 Sight glass
S7, S8 Shut-off valve
MV2 Magnet valve
MV1, MV3-5 Magnet valve
LM1 Evaporator with plate heat exchanger (for low pressure)
PV1, PV2 Expanding valve
M1 Blower evaporator
PC1 Double pressostat
PC2 Double pressostat
PC3 High pressure pressostat
PC4, PC5 High pressure pressostat
PE1, PE2 Steam trap
TR1 Thermostat FIG. 7B shows the second part of the cooling apparatus chart. Input pipe 708 is intended for coolant 109 of cooling apparatus 108 so that coolant 109 flows from a accumulator in input pipe 708 towards treatment chamber 102. If coolant 109 is generated from air, liquid nitrogen generator 603 may fill said accumulator. StirLIN-1 manufactured by Stirling Cryogenics is mentioned one example of liquid nitrogen generator 603.

Appropriate coolants for secondary cooling apparatus 107 are, for example, R-23 (RS-23) and R-404 (RS-404A).

In one embodiment system 101 is adapted to remove the coolant to be used in secondary cooling apparatus 107 from evaporator 110 before usage of cooling apparatus 108, i.e. before opening valve 111.

In addition to system 101, which is intended for cryogenic therapy and which is described in the above, the invention concerns use of system 101 in a cryogenic treatment that is targeted to at least one person.

System 101 is adapted to results in health effects that are based on cryogenic air and snow mist. The activation of brown fat is mentioned as one example. As generally known, a human body saves the energy, which is obtained from nutrition, by creating white fat. A human body further includes brown fat that affects metabolism and consumption of white fat. The brown fat is detected to activate due to the cryogenic therapy when snow mist is created in treatment chamber 102, and because of this activation the brown fat reduces the amount of the white fat. As another example of positive health effects of snow mist is that the cooperative action of the snow mist and the cryogenic air causes a human body to produce at least one of the following substances: endorphin, cortisone, testosterone, erythropoietin, or dopamine.

While the present invention has been described in connection with a number of exemplary embodiments, and implementations, the present invention is not so limited, but rather covers various modifications, and equivalent arrangements, which fall within the purview of prospective claims.

What is claimed is:

1. A system for cryotherapy, the system comprising
a treatment chamber for at least one person,
a closable entry to the treatment chamber, and
a cooling apparatus comprising an evaporator configured to function with a coolant and a valve for flow control of the coolant, the evaporator being placed in the treatment chamber and the valve being coupled to the evaporator,
the system further comprising
a ventilation aperture for obtaining an additional air into the treatment chamber, the ventilation aperture being placed far from the evaporator to such spot that the additional air flows from the ventilation aperture towards the centre of the treatment chamber and simultaneously mixes with an air included in the treatment chamber so that water vapour of the additional air changes from gas to solid ice crystals and forms snow mist in the treatment chamber, and
a secondary cooling apparatus and the valve is to be opened when due to use of the secondary cooling apparatus the air included in the treatment chamber is cooled down to a predetermined temperature, and
the system is configured to create the snow mist in response to opening the valve and flowing of the coolant into the evaporator wherein the coolant is a liquid nitrogen,
wherein the system comprises a mid-chamber which includes an entry to the treatment chamber and an aperture for obtaining the additional air through the mid-chamber into the treatment chamber.

2. The system as claimed in claim 1, wherein the system comprises such vestibule which includes an entry to the mid-chamber and a vent for obtaining the additional air through the vestibule into the mid-chamber.

3. The system as claimed in claim 1, wherein the system comprises a ventilation hatch, the ventilation hatch preventing in its closed position flowing of the additional air into the treatment chamber.

4. The system as claimed in claim 3, wherein the ventilation hatch is configured to be opened from its closed position before opening of the valve.

5. The system as claimed in claim 3, wherein the ventilation hatch is placed to one of the following spots: a door, between a door and a door frame, an outer wall of the system, another surface between the treatment chamber and a space surrounding the treatment chamber.

6. The system as claimed in claim 1, wherein the system comprises a piping for the coolant, the piping comprising a curved part whose wall thickness is greater than in a straight part of piping.

7. The system as claimed in claim 1, wherein the system comprises a liquid nitrogen generator and the system is configured to receive an ambient air and to produce the liquid nitrogen to be used as the coolant from the ambient air.

\* \* \* \* \*